(12) United States Patent
Fujiki et al.

(10) Patent No.: US 10,533,197 B2
(45) Date of Patent: Jan. 14, 2020

(54) METHOD FOR CULTURING MICROORGANISM, AND PROCESS FOR PRODUCING SUBSTANCE WITH MICROORGANISM

(75) Inventors: Tetsuya Fujiki, Osaka (JP); Shunsuke Sato, Takasago (JP)

(73) Assignee: KANEKA CORPORATION, Osaka (JP)

( * ) Notice: Subject to any disclaimer, the term of this patent is extended or adjusted under 35 U.S.C. 154(b) by 2576 days.

(21) Appl. No.: 13/260,145

(22) PCT Filed: Mar. 31, 2010

(86) PCT No.: PCT/JP2010/002354
§ 371 (c)(1),
(2), (4) Date: Dec. 6, 2011

(87) PCT Pub. No.: WO2010/113497
PCT Pub. Date: Oct. 7, 2010

(65) Prior Publication Data
US 2019/0071700 A1 Mar. 7, 2019

(30) Foreign Application Priority Data
Mar. 31, 2009 (JP) ................. 2009-086736

(51) Int. Cl.
| | | |
|---|---|---|
| C12N 15/74 | (2006.01) | |
| C12P 7/62 | (2006.01) | |
| C12P 7/64 | (2006.01) | |
| C12N 1/20 | (2006.01) | |

(52) U.S. Cl.
CPC .............. *C12P 7/6445* (2013.01); *C12N 1/20* (2013.01)

(58) Field of Classification Search
CPC ............. C12P 7/62; C12P 7/625; C12N 15/74
See application file for complete search history.

(56) References Cited

U.S. PATENT DOCUMENTS

| | | | | |
|---|---|---|---|---|
| 7,384,766 B2 * | 6/2008 | Maruyama | ............. | C12N 15/52 435/252.3 |
| 9,175,317 B2 * | 11/2015 | Sato | ............. | C12N 9/1029 |
| 2002/0086377 A1 | 7/2002 | Doi et al. | | |

FOREIGN PATENT DOCUMENTS

| | | |
|---|---|---|
| EP | 0533144 A2 | 3/1993 |
| EP | 1 557 470 * | 7/2005 |
| EP | 1557460 A1 | 7/2005 |
| JP | 2001-252069 A | 9/2001 |
| JP | 2001-340078 A | 12/2001 |
| WO | WO-2005085415 A1 | 9/2005 |

OTHER PUBLICATIONS

Palm Kernel Oil 2019; at en.wikipedia.org/wiki/Pal,_kernel_oil.*
Typical Fatty Acid Compositions of Some Common Fats 2019; at web.pdx.edu/wannserc/C336S12/fat.pdf.*
Cupriavidus necator. 2019; at en.wikipedia.org/wiki/Cupriavidus_ necator.*
Zhang et al. 2006; Engineering the monomer composition of polyhydroxyalkanoates synthesized in *Saccharomyces cerevisiae*. Applied and Environmental Microbiology. 72(1): 536-543.*
Lu et al. 2003; Enhanced production of poly(3hydroxybutyrate-co-3-hydroxyhexanoate) via manipulating the fatty acid beta-oxidation pathway in *E. coli*. FEMS Microbiology Letters. 221: 97-101.*
Kamilah et al. 2018; The use of palm oil-based waste cooking oil to enhance the production of polyhydroxybutyrate [P(3HB)] by cupriavidus necator H 16 strain. Arabian Journal of Science and Engineering. 43: 3453-3463.*
Viele et al. 2013; Esterification of high free faty acid crude palm kernel oil as feedstock for base-catalyzed transesterification reaction. Int, J of Applications or Innovation in Engineering Management. 2(12):361-365.*
Young et al. 1983; Palm kernel and coconut oils: Analytical characteristics, process technology and uses. JAOCS 60(2): 374-379.*
"BAA21815" T. Fukui, et al., GenBank, Aug. 19, 1997.
Loo et al., "Biosynthesis and characterization of poly(3-hydroxybutyrate-co-3-hydroxyhexanoate) from palm oil products in a *Wautersia eutropha* mutant", Biotechnology Letters (2005) 27: 1405-1410.
Chan et al., "Production of Medium-Chain-Length Polyhydroxyalkanoates by *Pseudomonas aeruginosa* With Fatty Acids and Alternative Carbon Sources", Applied Biochemistry and Biotechnology, vol. 129-132, 2006, pp. 933-941.
Database WPI Week 200224 Thomson Scientific, London, GB; AN 2002-181797 XP002688628 & JP 2001 252069A (NOF Corp) Sep. 18, 2001.
Sudesh et al., "Synthesis, structure and properties of polyhydroxyalkanoates: biological polyesters", Prog. Polym. Sci. 25 (2000) 1503-1555.
Communication from European Patent Office including Extended European Search Report issued in EP 10758276 dated Dec. 12, 2012.
Marsudi, S. et al., Palm Oil Utilization for the Simultaneous Production of Polyhydroxyalkanoates and Rhamnolipids by Pseudomonas Aeruginosa, Appl. Microbiol. Biotechnol., 2008, vol. 78, No. 6, pp. 955-961.
Impallomeni, G. et al., Tween 20 and Its Major Free Fatty Acids as Carbon Substrates for the Production of Polyhydroxyalkanoates in Pseudomonas Aeruginosa ATCC 27853., J. Polym. Environ., 2000, vol. 8, No. 2, pp. 97-102.
Tetsuya Fujiki et al., "Challenge for the Pracdtical use of Microbial Polyhydroxyalkanoate," CSJ: the Chemical Society of Japan Koen Yokoshu, 2009, vol. 89th, No. 2, p. 1242.

(Continued)

*Primary Examiner* — Karen Cochrane Carlson
(74) *Attorney, Agent, or Firm* — Polsinelli PC

(57) ABSTRACT

Using as a carbon source a long chain fatty acid which has not necessarily been efficaciously used in industry, culture of a microorganism and production of a substance by the microorganism are industrially efficiently carried out. A microorganism is cultured in the presence of a carbon source including anyone of the following compositions: (1) a fatty acid composition containing at least two fatty acids selected from the group consisting of lauric acid, myristic acid, palmitic acid and oleic acid; and (2) a mixed composition containing at least one fatty acid selected from the group consisting of lauric acid, myristic acid, palmitic acid and oleic acid, and a fat and oil, and having a content of the fatty acid of not less than 10% by weight.

13 Claims, No Drawings

Specification includes a Sequence Listing.

(56) References Cited

OTHER PUBLICATIONS

Seung Hwan Lee et al., "Production of Poly(3-Hydroxybutyrate-co-3-Hydroxyhexanoate) by High-Cell-Density Cultivation of *Aeromonas hydrophila*," Biotechnology and Bioengineering, vol. 67, No. 2, Jan. 20, 2000, pp. 240-244.

Regina V. Antonio et al., "Analysis of in vivo substrate specificity of the PHA synthase from *Ralstonia eutropha*: formation of novel copolyesters in recombinant *Escherichia coli*," FEMS Microbiology Letters 182 (2000) pp. 111-117.

* cited by examiner

SEQUENCE LISTING

<160> NUMBER OF SEQ ID NOS: 1

<210> SEQ ID NO 1
<211> LENGTH: 594
<212> TYPE: PRT
<213> ORGANISM: Aeromonas caviae

<400> SEQUENCE: 1

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

```
Pro Gln Asn Ser Leu Val Ala Trp Leu Val Ala Gln Gly Gln Thr Val
            260                 265                 270
Phe Met Ile Ser Trp Arg Asn Pro Gly Val Ala Gln Ala Gln Ile Asp
            275                 280                 285
Leu Asp Asp Tyr Val Val Asp Gly Val Ile Ala Ala Leu Asp Gly Val
            290                 295                 300
Glu Ala Ala Thr Gly Glu Arg Glu Val His Gly Ile Gly Tyr Cys Ile
305                 310                 315                 320
Gly Gly Thr Ala Leu Ser Leu Ala Met Gly Trp Leu Ala Ala Arg Arg
                325                 330                 335
Gln Lys Gln Arg Val Arg Thr Ala Thr Leu Phe Thr Thr Leu Leu Asp
                340                 345                 350
Phe Ser Gln Pro Gly Glu Leu Gly Ile Phe Ile His Glu Pro Ile Ile
                355                 360                 365
Ala Ala Leu Glu Ala Gln Asn Glu Ala Lys Gly Ile Met Asp Gly Arg
                370                 375                 380
Gln Leu Ala Val Ser Phe Ser Leu Leu Arg Glu Asn Ser Leu Tyr Trp
385                 390                 395                 400
Asn Tyr Tyr Ile Asp Ser Tyr Leu Lys Gly Gln Ser Pro Val Ala Phe
                405                 410                 415
Asp Leu Leu His Trp Asn Ser Asp Ser Thr Asn Val Ala Gly Lys Thr
                420                 425                 430
His Asn Ser Leu Leu Arg Arg Leu Tyr Leu Glu Asn Gln Leu Val Lys
                435                 440                 445
Gly Glu Leu Lys Ile Arg Asn Thr Arg Ile Asp Leu Gly Lys Val Lys
                450                 455                 460
Thr Pro Val Leu Leu Val Ser Ala Val Asp Asp His Ile Ala Leu Trp
465                 470                 475                 480
Gln Gly Thr Trp Gln Gly Met Lys Leu Phe Gly Gly Glu Gln Arg Phe
                485                 490                 495
Leu Leu Ala Glu Ser Gly His Ile Ala Gly Ile Ile Asn Pro Pro Ala
                500                 505                 510
Ala Asn Lys Tyr Gly Phe Trp His Asn Gly Ala Glu Ala Glu Ser Pro
                515                 520                 525
Glu Ser Trp Leu Ala Gly Ala Thr His Gln Gly Gly Ser Trp Trp Pro
                530                 535                 540
Glu Met Met Gly Phe Ile Gln Asn Arg Asp Glu Gly Ser Glu Pro Val
545                 550                 555                 560
Pro Ala Arg Val Pro Glu Glu Gly Leu Ala Pro Ala Pro Gly His Tyr
                565                 570                 575
Val Lys Val Arg Leu Asn Pro Val Phe Ala Cys Pro Thr Glu Glu Asp
                580                 585                 590
Ala Ala
```

METHOD FOR CULTURING MICROORGANISM, AND PROCESS FOR PRODUCING SUBSTANCE WITH MICROORGANISM

CROSS-REFERENCE TO RELATED APPLICATIONS

This application is a 35 U.S.C. 371 National Stage Application of International Application No. PCT/JP2010/002354, filed Mar. 31, 2010, claiming priority from Japanese Patent Application No. 2009-086736, filed Mar. 31, 2009, the entire contents of which are incorporated herein by reference in their entirety.

TECHNICAL FIELD

The present invention relates to a method for industrially efficiently culturing a microorganism or producing a substance by a microorganism using a long chain fatty acid as a carbon source which can be suitably utilized by a microorganism. Further, the present invention relates to a method for industrially efficiently producing polyhydroxyalkanoate (hereinafter, may be also referred to as PHA) by a microorganism using the carbon source.

BACKGROUND ART

Significance and importance of culture of microorganisms, and production of substances by microorganisms (fermentative production, bioconversion, etc.) are increasingly growing on the basis of increasing concerns for environmental issues, food issues, health and safety, as well as elevation of orientation for native or nature, and the like.

In culture of a microorganism and production of a substance by a microorganism, a carbon source suitably utilized by the microorganism (carbon source for culture, fermentation, etc.) is required. Typical examples of the carbon source include carbohydrate, fats and oils, short chain fatty acids, and the like.

In recent years, regenerable carbon sources (in particular, nonpetroleum-derived carbon source), and more preferably carbon sources that do not compete with food (non-edible carbon sources, generally referred to) have been increasingly demanded as carbon sources, on the basis of environmental issues and the like.

In this respect, long chain fatty acids (for example, long chain fatty acids derived from plants) are deemed to be a candidate for suitable carbon sources. Long chain fatty acids can be obtained from, for example, coconut, palm (including palm kernel), and the like. Plants such as coconut and palm have been known to include long chain fatty acids as constitutive fatty acids in fats and oils. Typical long chain fatty acids derived from these plants may include long chain saturated fatty acids such as lauric acid having 12 carbon atoms, myristic acid having 14 carbon atoms and palmitic acid having 16 carbon atoms, and long chain unsaturated fatty acids such as oleic acid having 18 carbon atoms.

These long chain fatty acids have been used as an industrial basic ingredient of surfactants, soaps, cosmetics and the like. However, they have not been widely used in industry that uses microorganisms. In particular, researches on use of these long chain fatty acids as a carbon source for culture of microorganisms and production of substances by microorganisms have not been sufficiently advanced.

Examples of producing PHA using lauric acid or oleic acid alone as a carbon source by culturing *Aeromonas hydrophila* were reported (see Nonpatent Document 1). However, examples in which oleic acid was used alone as a carbon source were principally investigated, and myristic acid and palmitic acid were not studied.

Although examples of producing PHA using lauric acid or myristic acid alone as a carbon source by culturing *Ralstonia eutropha* (see Patent Document 1) were reported, the amount of production of PHA is extremely low, not greater than 1 g/L. Also, palmitic acid was not used.

Moreover, examples of producing PHA using a salt such as sodium laurate alone as a carbon source by culturing *Escherichia coli* (see Nonpatent Document 2) were reported. However, myristic acid and palmitic acid were not used.

In the aforementioned researches, applicable culture scale remains within a small scale ranging several ml to several L.

As in the foregoing, there have been no prospects for possibility of industrially suitably using a variety of long chain fatty acids as a carbon source for culture of microorganisms and production of substances by microorganisms.

PRIOR ART DOCUMENTS

Patent Documents

Patent Document 1: U.S. Patent Application, Publication No. 2002/0086377

Nonpatent Documents

Nonpatent Document 1: Lee S., et. al., Biotechnol. Bioeng., 67: 240-244 (2000)
Nonpatent Document 2: Regina V., et. al., FEMS MICROBIOLOGY LETTERS, 111-117 (2000)

DISCLOSURE OF THE INVENTION

Problems to be Solved by the Invention

An object of the present invention is to provide a method of efficaciously using a long chain fatty acid which has not necessarily been efficaciously used in industry so far.

Specifically, an object of the invention is to provide a method for industrially efficiently culturing a microorganism and producing a substance by a microorganism using the long chain fatty acid as a carbon source which can be suitably utilized by the microorganism. In addition, another object of the invention is to provide a method for industrially efficiently producing PHA using the carbon source.

Means for Solving the Problems

The present inventors preliminary investigated utilization of each fatty acid of lauric acid, myristic acid and palmitic acid by a microorganism through culturing *Escherichia coli* using each of the fatty acid alone as a carbon source. As a result, utilization of each of myristic acid and palmitic acid was extremely low, and use of these as a carbon source was believed to be very difficult. Also, satisfactory utilization of lauric acid was not necessarily exhibited.

Therefore, the present inventors thoroughly investigated lauric acid, myristic acid and palmitic acid that are long chain fatty acids, which are not sufficiently utilized by microorganisms, for suitably using in culture of a microorganism and in production of a substance by a microorganism.

As a result, it was found that a composition containing a plurality of long chain fatty acids, or a mixed composition of a long chain fatty acid, and a fat and oil can be extremely suitably used as a carbon source for culture of a microorganism and production of a substance by a microorganism (for example, production of PHA). Accordingly, the present invention was accomplished.

More specifically, according to an aspect of the present invention, a method for culturing a microorganism is provided which includes the step of culturing a microorganism in the presence of a carbon source including any one of the following compositions:

(1) a fatty acid composition containing at least two fatty acids selected from the group consisting of lauric acid, myristic acid, palmitic acid and oleic acid; and (2) a mixed composition containing at least one fatty acid selected from the group consisting of lauric acid, myristic acid, palmitic acid and oleic acid, and a fat and oil, and having a content of the fatty acid of not less than 10% by weight.

It is preferred that the fatty acid composition contains at least one selected from the group consisting of lauric acid, myristic acid and palmitic acid, and oleic acid, whereas the mixed composition contains at least one selected from the group consisting of lauric acid, myristic acid and palmitic acid, oleic acid, and a fat and oil.

It is preferred that the fatty acid composition contains lauric acid, and oleic acid, whereas
the mixed composition contains lauric acid, oleic acid, and a fat and oil.

It is preferred that the fatty acid composition contains palmitic acid, and oleic acid, whereas
the mixed composition contains palmitic acid, oleic acid, and a fat and oil.

It is preferred that the fatty acid composition contains at least three selected from the group consisting of lauric acid, myristic acid, palmitic acid and oleic acid, whereas
the mixed composition contains at least three selected from the group consisting of lauric acid, myristic acid, palmitic acid and oleic acid, and a fat and oil.

It is preferred that the fatty acid composition contains at least two selected from the group consisting of lauric acid, myristic acid and palmitic acid, and oleic acid, whereas
the mixed composition contains at least two selected from the group consisting of lauric acid, myristic acid and palmitic acid, oleic acid, and a fat and oil.

It is preferred that the fatty acid composition contains lauric acid, palmitic acid, and oleic acid, whereas
the mixed composition contains lauric acid, palmitic acid, oleic acid, and a fat and oil.

It is preferred that the fatty acid composition contains lauric acid, myristic acid, palmitic acid, and oleic acid, whereas
the mixed composition contains lauric acid, myristic acid, palmitic acid, oleic acid, and a fat and oil.

It is preferred that the content of long chain saturated fatty acid(s) in long chain fatty acid(s) included in the fatty acid composition or the mixed composition be not less than 20% by weight.

It is preferred that the total content of myristic acid and palmitic acid in the long chain fatty acids included in the fatty acid composition or the mixed composition be not less than 5% by weight.

It is preferred that the fatty acid composition or the mixed composition has an ascending melting point of not higher than a temperature that is greater than the culture temperature by 10° C.

It is preferred that the content of the fatty acid in the mixed composition be not less than 45% by weight.

It is preferred that the microorganism be a bacterium.
It is preferred that the microorganism be a microorganism belonging to genus *Cupriavidus* or genus *Esherichia*.
It is preferred that the microorganism be a microorganism belonging to genus *Cupriavidus*.
It is preferred that the microorganism be *Cupriavidus necator*.
It is preferred that the microorganism be *Cupriavidus necator* incorporating:
a polyhydroxyalkanoate synthase gene encoding an amino acid sequence shown in SEQ ID NO: 1; or
a polyhydroxyalkanoate synthase gene encoding a polypeptide having a sequence identity to the amino acid sequence of not less than 85%, and having a synthetic activity of polyhydroxyalkanoate.
It is preferred that the microorganism be a microorganism belonging to genus *Esherichia*.
It is preferred that the microorganism be *Esherichia coli*.
It is preferred that the microorganism be yeast.

Furthermore, the present invention also relates to a method for producing a metabolic product of a microorganism, the method comprising the steps of
culturing the microorganism in the presence of a carbon source including any of the aforementioned compositions, and
recovering the metabolic product produced by the microorganism cultured.

It is preferred that the metabolic product of the microorganism be polyhydroxyalkanoate.

It is preferred that the polyhydroxyalkanoate be a copolymer of 3-hydroxybutyric acid and 3-hydroxyhexanoic acid.

Effects of the Invention

According to the present invention, efficacious use of long chain fatty acids, particularly long chain saturated fatty acids, which have not necessarily been efficaciously used in industry so far, is enabled. Specifically, by using the long chain fatty acids, particularly the long chain saturated fatty acids as a carbon source which can be suitably utilized by a microorganism, industrially efficient culture of the microorganism and production of a substance by the microorganism are enabled. In addition, industrially efficient production of PHA is enabled using the carbon source.

MODE FOR CARRYING OUT THE INVENTION

Hereinafter, the present invention is explained in detail.
In culture of a microorganism and production of a substance by a microorganism, generally, carbohydrates such as glucose and sucrose have been widely used as a carbon source. These carbohydrates are superior in utilization efficiency as a carbon source since they are dissolved in a liquid such as a culture liquid in which the microorganisms are grown under common culture conditions due to having high solubility in water. On the other hand, carbon sources having low solubility in water have, in general, low utilization efficiency (utilization) by microorganisms. The present inventors ascertained that long chain fatty acids having very low solubility in water, particularly, long chain saturated fatty acids (in particular, myristic acid and palmitic acid) exhibit extremely low utilization by microorganisms.

In addition, investigation of utilization of mixtures of lauric acid, myristic acid or palmitic acid with a fat and oil indicated that utilization decreases as the content of fatty acids in the mixture increases.

However, these fatty acids can be extremely efficaciously used as a carbon source according to the present invention.

The carbon source in the present invention includes any one of the following compositions:

(1) a fatty acid composition containing at least two fatty acids selected from the group consisting of lauric acid, myristic acid, palmitic acid and oleic acid; and (2) a fatty acid-fat and oil mixed composition containing at least one fatty acid selected from the group consisting of lauric acid, myristic acid, palmitic acid and oleic acid, and a fat and oil, and having a content of the fatty acid of not less than 10% by weight.

According to the present invention, use in combination of various types of fatty acid having low utilization or a fat and oil as a carbon source enables the utilization to be improved, and thus the present invention is very significant in terms of enabling these fatty acids to be efficaciously used.

The fat and oil which can be used in the fatty acid-fat and oil mixed composition (2) is not particularly limited, and a fat and oil containing lauric acid, myristic acid, palmitic acid or oleic acid as a constitutive component is preferred. Specific examples include a fat and oil derived from palm, coconut, corn, soybean, rapeseed, olive, Jatropha, and the like.

The content of the fatty acid in the fatty acid-fat and oil mixed composition (2) is not less than 10% by weight in light of improvement of the utilization, and effective use of the fatty acid. The content of the fatty acid is preferably not less than 20% by weight, more preferably not less than 30% by weight, still more preferably not less than 40% by weight, particularly preferably not less than 45% by weight, and most preferably not less than 50% by weight. The upper limit of the content is not limited, and may be less than 100% by weight. The content of the fatty acid as referred to herein means a weight ratio of the fatty acid to the total amount of the fatty acid and the fat and oil (the "fatty acid" as intended herein does not include the fatty acid constituting the aforementioned fat and oil).

According to one suitable embodiment of the present invention, the fatty acid composition (1) or the mixed composition (2) contains oleic acid, and also contains at least one selected from the group consisting of lauric acid, myristic acid and palmitic acid. Oleic acid that is a long chain unsaturated fatty acid not only exhibits high utilization per se by a microorganism, but also has an effect of improving utilization of lauric acid, myristic acid and palmitic acid that are long chain saturated fatty acids. Therefore, by using oleic acid in combination with the long chain saturated fatty acid, effective use of the long chain saturated fatty acid is enabled, and in addition high utilization can be synergistically attained.

In light of effective use of the long chain saturated fatty acid, the content of the long chain unsaturated fatty acid relative to the long chain fatty acid (the long chain saturated fatty acid and the long chain unsaturated fatty acid in total) in the fatty acid composition (1) or the mixed composition (2) is preferably not less than 20% by weight, more preferably not less than 30% by weight, still more preferably not less than 40% by weight, and particularly preferably not less than 50% by weight. Herein, the content of the long chain unsaturated fatty acid relative to the long chain fatty acid means the weight ratio of the long chain saturated fatty acid relative to the total amount of the long chain saturated fatty acid and the long chain unsaturated fatty acid used in the fatty acid composition (1) or the mixed composition (2). It is to be noted that when the content is calculated, a long chain saturated fatty acid and a long chain unsaturated fatty acid constituting the fat and oil are not taken into consideration. Herein, the long chain saturated fatty acid may indicate lauric acid, myristic acid and palmitic acid, whereas the long chain unsaturated fatty acid may indicate oleic acid.

More suitably, the fatty acid composition. (1) or the mixed composition (2) contains oleic acid, and also contains lauric acid or palmitic acid.

According to an other suitable embodiment of the present invention, the fatty acid composition (1) or the mixed composition (2) contains at least three fatty acids selected from the group consisting of lauric acid, myristic acid, palmitic acid and oleic acid. More suitably, the fatty acid composition (1) or the mixed composition (2) contains oleic acid, and also contains at least two selected from the group consisting of lauric acid, myristic acid and palmitic acid. More suitably, the fatty acid composition (1) or the mixed composition (2) contains lauric acid, palmitic acid and oleic acid, and particularly-suitably contains lauric acid, myristic acid, palmitic acid and oleic acid.

In light of efficacious use of myristic acid and palmitic acid that exhibit particularly low utilization, the fatty acid composition (1) or the mixed composition (2) preferably contains myristic acid and/or palmitic acid. In this instance, the total content of myristic acid and palmitic acid in the long chain fatty acids included in the fatty acid composition (1) or the mixed composition (2) is preferably not less than 5% by weight. The total content is more preferably not less than 10% by weight, and still more preferably not less than 15% by weight. The upper limit of the total content is not particularly limit, and is preferably not greater than 70% by weight, more preferably not greater than 65% by weight, still more preferably not greater than 60% by weight, and particularly preferably not greater than 55% by weight for further improving the utilization.

According to yet another suitable embodiment of the present invention, the fatty acid composition (1) or the mixed composition (2) of the present invention has an ascending melting point of not higher than a temperature that is greater than the culture temperature of the microorganism by 10° C. (i.e., being not higher than the culture temperature of the microorganism +10° C.). The ascending melting point is more preferably not higher than the culture temperature of the microorganism +9° C., still more preferably not higher than the culture temperature of the microorganism +8° C., and particularly preferably not higher than the culture temperature of the microorganism +7° C. Optimal growth temperature of many of microorganisms industrially used is generally not higher than 37° C. Therefore, in many cases, the fatty acid composition (1) or the mixed composition (2) of the present invention has an ascending melting point of preferably not higher than 47° C. The ascending melting point is more preferably not higher than 46° C., still more preferably not higher than 45° C., and particularly preferably not higher than 44° C. However, the ascending melting point of the composition used in the present invention is not limited to the values described above. The ascending melting point may be predetermined appropriately depending on the culture temperature of the microorganism, and a composition that satisfies this requirement may be obtained. The lower limit of the ascending melting point is not particularly defined.

The present inventors elucidated the ascending melting points of the long chain saturated fatty acids to be about 43° C. for lauric acid, about 52° C. for myristic acid, about 62° C. for palmitic acid, and the ascending melting point of oleic acid that is a long chain unsaturated fatty acid to be about 12° C. According to the present invention, when a plurality of the fatty acids are included, the ascending melting point of the composition can be appropriately regulated to meet the growth temperature of the microorganism, and the utilization by the microorganism can be improved. Also in the case of myristic acid and palmitic acid having a high ascending melting point, such effects of the present invention can be suitably exerted. Surprisingly, even in the case of a composition that exhibits a solid state at culture temperatures, it can be efficaciously used as a carbon source.

In the present invention, the ascending melting point of the fatty acid composition (1) or the mixed composition (2) may be determined according to the following procedures.

(1) One end of a capillary (internal diameter: 1 mm, external diameter: not greater than 2 mm, length: 50 to 80 mm) with two open ends is dipped into a completely melted sample to fill in the capillary with the sample to a level of about 10 mm, and then quickly harden the sample inside the capillary with ice piece or the like.

(2) The capillary including the hardened sample is left to stand at not higher than 10° C. for 24 hours, or on ice for 1 hour and thereafter subjected to the test.

(3) The capillary is set in an ascending melting point analyzer (manufactured by ELEX SCIENTIFIC Co., Ltd., EX-871A).

(4) The capillary is dipped in a vessel filled with water having a temperature lower than the predicted melting point by about 20° C., and the bottom end of the thermometer is placed at a level of 30 mm below the water surface.

(5) Heating water in the vessel such that the water temperature is elevated initially at a rate of 2° C./rain while stirring by an appropriate method.

(6) Heating is continued such that the water temperature is elevated at a rate of 0.5° C./min after the temperature reaches lower than the predicted melting point by 10° C.

(7) The temperature at which the sample starts ascending in the capillary is determined as the ascending melting point.

Specific constitution of the fatty acid composition (1) and the mixed composition (2) of the present invention may vary depending on the type of the microorganism employed, the type of the substance produced by the microorganism, various conditions of the culture (medium components, pH, culture temperature, etc.) and the like; therefore it cannot necessarily be uniformly defined. However, some suitable constitutions can be exemplified. One of the suitable constitutions contains lauric acid at a content of 30 to 70% by weight, myristic acid at a content of 5 to 30% by weight, palmitic acid at a content of 5 to 30% by weight, and oleic acid at a content of 10 to 30% by weight. One of suitable constitutions contains lauric acid at a content of 10 to 40% by weight, 0 to 10% by weight of myristic acid, 20 to 40% by weight of palmitic acid, and 30 to 50% by weight of oleic acid. One of suitable constitutions contains lauric acid at a content of 15 to 45% by weight, palmitic acid at a content of 15 to 45% by weight, and oleic acid at a content of 20 to 50% by weight. The value of the contents described above indicates the proportion of the fatty acids contained in the composition (the term "fatty acid" as intended herein does not include the fatty acid constituting the fat and oil) with respect to the total amount. In connection with the mixed composition (2), the aforementioned content is for the value excluding the fat and oil.

However, the constitutions described above are merely examples of suitable constitutions, and the present invention is not limited to the aforementioned constitutions. Also, to the constitution may be added a fat and oil as needed.

The carbon source including the fatty acid composition (1) or the mixed composition (2) of the present invention may further contain other fatty acid, as well as a carbohydrate, protein, amino acid, and the like.

Examples of metabolite (the metabolic product) of the microorganism obtained by allowing for production by the microorganism through culturing the microorganism according to the present invention include e.g., alcohols such as ethanol, butanol and propanol, acids such as lactic acid, acetic acid, amino acid and nucleic acid, lipids, fats and oils as well as polyhydroxyalkanoate (PHA), and the like. PHA is a thermoplastic polyester produced and accumulated in cells of many microorganism spices as an energy storage material, and is biodegradable. At present, non-petroleum plastics have attracted attention due to increasing environmental consciousness, and in particular, PHA produced by microorganisms and accumulated in their cellular bodies is expected to have small adverse effects on ecological system since it is incorporated into the process of carbon cycle of the natural world. Accordingly, putting PHA into practical applications has been desired. Therefore, PHA is one preferable example of substances to be produced according to the present invention.

The type of PHA is not particularly limited as long as it is produced by a microorganism, but PHA formed by polymerization of one monomer selected from 3-hydroxyalkanoic acid having 4 to 16 carbon atoms, and copolymerized PHA formed by copolymerization of two or more monomers selected from 3-hydroxyalkanoic acid having 4 to 16 carbon atoms are preferred. Examples of such PHA include polyhydroxybutyrate (PHB) constituted with 3-hydroxyalkanoic acid having 4 carbon atoms, polyhydroxybutyrate hexanoate (PHBH) constituted with 3-hydroxyalkanoic acids each having 4 and 6 carbon atoms, polyhydroxybutyrate valerate (PHBV) constituted with 3-hydroxyalkanoic acids each having 4 and 5 carbon atoms, polyhydroxyalkanoate (PHA) constituted with 3-hydroxyalkanoic acids having 4 to 14 carbon atoms, and the like.

The microorganism used in the culture of a microorganism, and in the production of a useful substance by a microorganism according to the present invention is not particularly limited, and any of microorganisms isolated from natural sources, microorganisms obtained by gene manipulation, and the like can be suitably used. Specifically, bacteria belonging to genus *Ralstonia*, genus *Cupriavidus*, genus *Wautersia*, genus *Aeromonas*, genus *Esherichia*, genus *Alcaligenes*, genus *Pseudomonas*, genus *Bacillus*, genus *Azotobacter*, genus *Nocardia*, genus *Sphingomonas*, genus *Comamonas* and the like, as well as yeasts belonging to genus *Saccharomyces*, genus *Yarrowia*, genus *Candida* and the like may be preferably used. As a matter of course, mutant strains obtained by subjecting the microorganism to an artificial mutation process, and strains mutated by a genetic engineering procedure may be also used.

Examples of the microorganism which may be used in producing PHA include those belonging to e.g., genus *Cupriavidus* such as *Cupriavidus necator*, genus *Alcaligenes* such as *Alcaligenes latas*, genus *Pseudomonas* such as *Pseudomonas putida, Pseudomonas fluorescens, Pseudomonas aeruginosa, Pseudomonas resinovorans* and *Pseudomonas oleovorans*, genus *Bacillus* such as *Bacillus megaterium*, genus *Azotobacter*, genus *Nocardia*, genus *Aeromonas* such as *Aeromonas caviae* and *Aeromonas hydrophila*, genus *Ralstonia*, genus *Wautersia*, genus *Comamonas*, and the like (see Microbiological Reviews, pp. 450-472, 1990). Biological cells artificially modified to produce PHA by introducing a PHA synthase gene or the like with a genetic engineering procedure may be also used. For example, gram negative bacteria such as those belonging to genus *Esheri-*

*chia*, gram positive bacteria such as those belonging to genus *Bacillus*, yeasts such as those belonging to genus *Saccharomyces*, genus *Yarrowia* and genus *Candida*, and cells of higher organisms such as plants may be also used; however, in light of possibility of accumulation of a large amount of PHA, microorganisms are preferably used.

When PHBH, a copolymer of 3-hydroxybutyric acid and 3-hydroxyhexanoic acid, that is one of PHA is produced, for example, a microorganism that originally produces PHBH such as *Aeromonas caviae* or *Aeromonas hydrophila* may be used, or biological cells artificially modified to produce PHBH by introducing a polyhydroxyalkanoate synthase gene or the like using a genetic engineering procedure into a microorganism that does not originally produce PHBH may be used. As a host microorganism into which the gene is introduced, for example, *Cupriavidus necator* maybe suitably used. Also, as the polyhydroxyalkanoate synthase gene, polyhydroxyalkanoate synthase gene derived from *Aeromonas caviae* or *Aeromonas hydrophila*, or a modified product of the same maybe used. The modified product which may be used includes a base sequence encoding polyhydroxyalkanoate synthase and the like having deletion, addition, insertion, or substitution of amino acid group(s) of polyhydroxyalkanoate synthase derived from a natural source. Specifically, *Cupriavidus necator* incorporating a polyhydroxyalkanoate synthase gene encoding an amino acid sequence shown in SEQ ID NO: 1, or a polyhydroxyalkanoate synthase gene encoding a polypeptide having a sequence identity of not less than 85% to the above amino acid sequence and having a synthetic activity of polyhydroxyalkanoate may be used.

For culturing a microorganism according to the present invention, a method in which a carbon source is added to a medium may be used. The medium composition, addition method of the carbon source, culture scale, conditions of aeration and stirring, as well as culture temperature, and culture time maybe determined ad libitum depending on the type of the microorganism to be cultured, and are not particularly limited. Continuously or intermittently adding a carbon source to the medium is preferred. The carbon source in the present invention may be a mixture prepared prior to adding to the medium, or each of constitutive components may be separately added to and mixed in the medium.

In the method for producing a metabolic product, such as PHA, of a microorganism according to the present invention, the metabolic product of the microorganism may be accumulated in the microorganism by the culture method described above, and thereafter, the metabolic product of the microorganism may be recovered from the cellular bodies using a known method. When the metabolic product of the microorganism is PHA, for example, the procedures described below may be employed. After completing the culture, cellular bodies are separated from the culture liquid by centrifugal separator or the like, and the cellular bodies are washed with distilled water and an organic solvent such as methanol, followed by drying. PHA is extracted from the dry cellular bodies using an organic solvent such as chloroform. The cellular components are removed by filtration or the like from the solution containing PHA, and a poor solvent such as methanol or hexane is added to the filtrate, whereby precipitation of PHA is permitted. Furthermore, after removing the supernatant liquid by filtration or centrifugal separation, PHA may be recovered by drying.

The present inventors confirmed that the aspect of the present invention can be suitably carried out in a culture scale of 2.5 L, and can be suitably repeated even in a scale of not less than 16,000 L. The achievement of such an increase in the scale by not less than 5,000 times suggests that the effects of the present invention can be suitably and maximally exerted even in greater industrial scale production.

In the present invention, improvement of utilization achievable by using the fatty acid composition (1) or the mixed composition (2) as a carbon source means that utilization of long chain saturated fatty acid that is less likely to be utilized is improved than the case in which the same is used alone by including a plurality of types of the long chain saturated fatty acids that are less likely to be utilized (lauric acid, myristic acid or palmitic acid), or by including both the long chain saturated fatty acid that is less likely to be utilized and a long chain unsaturated fatty acid that is likely to be utilized (oleic acid). Alternatively, the aforementioned improvement means that utilization of the long chain saturated fatty acid that is less likely to be utilized is improved than the case in which the same is used alone by including the long chain saturated fatty acid that is less likely to be utilized, and a fat and oil. Also, improvement of the utilization in the Present invention means consumption of the carbon source per unit time increases, and as a result, the amount of production of cellular bodies of a microorganism and the amount of production of the substance produced by the microorganism increases.

The amount of production of cellular bodies of a microorganism may be determined by a well-known method such as an optical density method, and a method of measuring the weight of dry cellular bodies. The amount of the substance produced by a microorganism may be measured by a well-known method such as a GC method or an HPLC method. The content of PHA accumulated in cells may be determined according to the method of Kato et al. (Appl. MicroBiol. Biotechnol., Vol. 45, page 363, (1996); Bull. Chem. Soc., Vol. 69, page 515 (1996)), by extracting from culture cells using an organic solvent such as chloroform, and then drying.

EXAMPLES

Hereinafter, the present invention is explained in more detail by way of Examples. However, the present invention is not limited to these Examples.

The ascending melting point of each composition was calculated according to the method described above.

Example 1

Culture of *Escherichia coli*

Using a variety of carbon sources, an *E. coli* HB101 strain (manufactured by Takara Bio Inc.) was cultured. An LB medium (10 g/L Bacto-tryptone, 5 g/L Bacto-yeast extract, and 5 g/L NaCl) was used as a preculture medium. For growth test, an M9 medium (6 g/L $Na_2HPO_4$, 3 g/L $KH_2PO_4$, 0.5 g/L NaCl, 1 g/L $NH_4Cl$, 1 mM $MgSO_4$, 0.001 w/v % Thiamine, and 0.1 mM $CaCl_2$) was used.

A glycerol stock of *E. coli* was inoculated into the preculture medium, and cultured at 37° C. for 12 hrs to execute preculture. Thereafter, the preculture liquid was inoculated at 2 v/v % into a 500-ml Sakaguchi flask containing 50 ml of the M9 medium. Next, various types of fatty acid compositions shown in Table 1 were each charged as a carbon source into the Sakaguchi flask at a concentration of 0.25 w/v %, and the mixture was cultured by shaking at 37° C. for 96 hrs. The carbon source was added batchwise into the Sakaguchi flask. After completing the culture, the cellular bodies were recovered by centrifugal separation, washed with methanol, freeze-dried, and then the weight of dry cellular bodies was measured. The results are shown in Table 1.

TABLE 1

|  | CS | Fatty acid and fat and oil constitution of CS | | | | | Results of culture | |
|---|---|---|---|---|---|---|---|---|
|  |  | LA content (wt %) | MA content (wt %) | PA content (wt %) | OA content (wt %) | Fat and oil content (wt %) | Ascending melting point (° C.) | Weight of dry cellular bodies (g/L) |
| Comparative Example 1 | LA | 100 | 0 | 0 | 0 | 0 | 43 | 2.11 |
|  | MA | 0 | 100 | 0 | 0 | 0 | 52 | 1.16 |
|  | PA | 0 | 0 | 100 | 0 | 0 | 62 | 1.02 |
|  | OA | 0 | 0 | 0 | 100 | 0 | 12 | 2.31 |
| Example 1 | CS 1 | 90 | 0 | 0 | 10 | 0 | 41 | 2.24 |
|  | CS 2 | 50 | 0 | 0 | 50 | 0 | 27 | 2.38 |
|  | CS 3 | 0 | 70 | 0 | 30 | 0 | 45 | 2.08 |
|  | CS 4 | 0 | 50 | 0 | 50 | 0 | 37 | 2.29 |
|  | CS 5 | 0 | 0 | 40 | 60 | 0 | 44 | 2.02 |
|  | CS 6 | 0 | 0 | 20 | 80 | 0 | 27 | 2.36 |
|  | CS 7 | 25 | 75 | 0 | 0 | 0 | 47 | 1.82 |
|  | CS 8 | 75 | 25 | 0 | 0 | 0 | 34 | 2.40 |
|  | CS 9 | 40 | 0 | 60 | 0 | 0 | 47 | 1.88 |
|  | CS 10 | 75 | 0 | 25 | 0 | 0 | 37 | 2.33 |
|  | CS 11 | 0 | 50 | 50 | 0 | 0 | 47 | 1.74 |
|  | CS 12 | 0 | 0 | 47 | 53 | 0 | 45 | 2.10 |
|  | CS 13 | 15 | 0 | 40 | 45 | 0 | 43 | 2.21 |
|  | CS 14 | 60 | 0 | 19 | 21 | 0 | 32 | 2.35 |
|  | CS 15 | 50 | 20 | 10 | 20 | 0 | 26 | 2.40 |
|  | CS 16 | 25 | 10 | 30 | 35 | 0 | 36 | 2.37 |
|  | CS 17 | 75 | 3 | 2 | 20 | 0 | 37 | 2.30 |

LA: Lauric acid,
MA: Myristic acid,
PA: Palmitic acid,
OA: Oleic acid,
CS: Carbon source Comparative Example 1

*Escherichia coli* was cultured under the same conditions as in Example 1 except that lauric acid, myristic acid, palmitic acid, or oleic acid was used as a carbon source in place of the various types of fatty acid composition, and the weight of dry cellular bodies was measured. The results are shown in Table 1.

Example 2

Culture of C. necator PHB-4 Strain

Using a variety of carbon sources, *Cupriavidus necator* PHB-4 strain (DSM541, available from DSMZ) was cultured. This strain does not synthesize PHA.

The composition of the preculture medium was constituted with 1 w/v % Meat-extract, 1 w/v % Bacto-tryptone, 0.2 w/v % Yeast-extract, 0.9 w/v % $Na_2HPO_4.12H_2O$ and 0.15 w/v % $KH_2PO_4$, and the pH was adjusted to 6.8.

The composition of the growth test medium was constituted with 1.1 w/v % $Na_2HPO_4.12H_2O$, 0.19 w/v % $KH_2PO_4$, 1.29 w/v % $(NH_4)_2SO_4$, 0.1 w/v % $MgSO_4.7H_2O$, and a 0.5 v/v % trace mineral salt solution (1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$ and 0.012 w/v % $NiCl_2.6H_2O$ dissolved in 0.1 N hydrochloric acid).

A glycerol stock of the *Cupriavidus necator* PHB-4 strain was inoculated into the preculture medium, and cultured at 30° C. for 12 hrs to execute preculture. Thereafter, the preculture liquid was inoculated at 2 v/v % into a 500-ml Sakaguchi flask containing 50 ml of the growth test medium. Next, various types of fatty acid compositions shown in Table 2 were each charged as a carbon source into the Sakaguchi flask at a concentration of 1.0 w/v %, and the mixture was cultured by shaking at 30° C. for 24 hrs. The carbon source was added batchwise into the Sakaguchi flask. After completing the culture, the cellular bodies were recovered by centrifugal separation, washed with methanol, freeze-dried, and then the weight of dry cellular bodies was measured. The results are shown in Table 2.

TABLE 2

|  | CS | Fatty acid and fat and oil constitution CS | | | | | Results of culture | |
|---|---|---|---|---|---|---|---|---|
|  |  | LA content (wt %) | MA content (wt %) | PA content (wt %) | OA content (wt %) | Fat and oil content (wt %) | Ascending melting point (° C.) | Weight of dry cellular bodies (g/L) |
| Comparative Example 2 | LA | 100 | 0 | 0 | 0 | 0 | 43 | 3.63 |
|  | MA | 0 | 100 | 0 | 0 | 0 | 52 | 1.91 |
|  | PA | 0 | 0 | 100 | 0 | 0 | 62 | 1.77 |
|  | OA | 0 | 0 | 0 | 100 | 0 | 12 | 4.54 |

TABLE 2-continued

| | | Fatty acid and fat and oil constitution CS | | | | | Results of culture | |
|---|---|---|---|---|---|---|---|---|
| | CS | LA content (wt %) | MA content (wt %) | PA content (wt %) | OA content (wt %) | Fat and oil content (wt %) | Ascending melting point (° C.) | Weight of dry cellular bodies (g/L) |
| Example 2 | CS 1 | 90 | 0 | 0 | 10 | 0 | 41 | 3.94 |
| | CS 2 | 50 | 0 | 0 | 50 | 0 | 27 | 4.57 |
| | CS 3 | 0 | 70 | 0 | 30 | 0 | 45 | 3.55 |
| | CS 4 | 0 | 50 | 0 | 50 | 0 | 37 | 4.33 |
| | CS 5 | 0 | 0 | 40 | 60 | 0 | 44 | 3.71 |
| | CS 6 | 0 | 0 | 20 | 80 | 0 | 27 | 4.51 |
| | CS 7 | 25 | 75 | 0 | 0 | 0 | 47 | 3.31 |
| | CS 8 | 75 | 25 | 0 | 0 | 0 | 34 | 4.46 |
| | CS 9 | 40 | 0 | 60 | 0 | 0 | 47 | 3.40 |
| | CS 10 | 75 | 0 | 25 | 0 | 0 | 37 | 4.18 |
| | CS 11 | 0 | 50 | 50 | 0 | 0 | 47 | 3.16 |
| | CS 12 | 0 | 0 | 47 | 53 | 0 | 45 | 3.62 |
| | CS 13 | 15 | 0 | 40 | 45 | 0 | 43 | 4.11 |
| | CS 14 | 60 | 0 | 19 | 21 | 0 | 32 | 4.50 |
| | CS 15 | 50 | 20 | 10 | 20 | 0 | 26 | 4.63 |
| | CS 16 | 25 | 10 | 30 | 35 | 0 | 36 | 4.49 |
| | CS 17 | 75 | 3 | 2 | 20 | 0 | 37 | 4.22 |

LA: Lauric acid,
MA: Myristic acid,
PA: Palmitic acid,
OA: Oleic acid,
CS: Carbon source Comparative Example 2

The *C. necator* PHB-4 strain was cultured under the same conditions as in Example 2 except that lauric acid, myristic acid, palmitic acid, or oleic acid was used as a carbon source in place of the various types of fatty acid composition, and the weight of dry cellular bodies was measured. The results are shown in Table 2.

Example 3

Production of PHA by Culture of *Pseudomonas resinovorans*

Using a variety of carbon sources, PHA was produced by culturing the microorganism.
The microorganism used was a *Pseudomonas resinovorans* ATCC 14235 strain (available from ATCC).
The composition of a mother culture medium was constituted with 1 w/v % Meat-extract, 1 w/v % Bacto-tryptone, 0.2 w/v % Yeast-extract, 0.9 w/v % $Na_2HPO_4.12H_2O$ and 0.15 w/v % $KH_2PO_4$, and the pH was adjusted to 6.8.
The composition of the preculture medium was constituted with 1.1 w/v % $Na_2HPO_4.12H_2O$, 0.19 w/v % $KH_2PO_4$, 1.29 w/v % $(NH_4)_2SO_4$, 0.1 w/v % $MgSO_4.7H_2O$, 2.5 w/v % palm olein oil and a 0.5 v/v % trace mineral salt solution (1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$ and 0.012 w/v % $NiCl_2.6H_2O$ dissolved in 0.1 N hydrochloric acid). Palm olein oil as a carbon source in the preculture medium was added batchwise at a concentration of 10 g/L.
The composition of the production medium of PHA was constituted with 0.385 w/v % $Na_2HPO_4.12H_2O$, 0.067 w/v % $KH_2PO_4$, 0.291 w/v % $(NH_4)_2SO_4$, 0.1 w/v % $MgSO_4.7H_2O$, a 0.5 v/v % trace mineral salt solution (1.6 w/v % $FeCl_3.6H_2O$, 1 w/v % $CaCl_2.2H_2O$, 0.02 w/v %, $CoCl_2.2H_2O$, 0.016 w/v % $CuSO_4.5H_2O$ and 0.012 w/v % $NiCl_2.6H_2O$ dissolved in 0.1 N hydrochloric acid), and 0.05 w/v % BIOSPUREX 200K (defoaming agent: manufactured by Cognis Japan Ltd.).

First, a glycerol stock (50 μl) of the *Pseudomonas resinovorans* ATCC 14.235 strain was inoculated into the mother culture medium (10 ml), and cultured for 24 hrs to execute mother culture. Thereafter, the mother culture liquid was inoculated at 1.0 v/v % into a 3-L jar fermenter (manufactured by B. E. MARUBISHI Co., Ltd., model MDL-300) containing 1.8 L of the preculture medium. The operating conditions involved a culture temperature of 30° C., a stirring rate of 500 rpm, and an aeration rate of 1.8 L/min. The preculture was executed by culturing for 24 hrs while controlling the pH to range from 6.7 to 6.8. For controlling the pH, a 7% aqueous ammonium hydroxide solution was used.
Next, the preculture liquid was inoculated at 5.0 v/v % into a 10-L jar fermenter (manufactured by B. E. MARUBISHI Co., Ltd., model MDL-1000) containing 6 L of the production medium. The operating conditions involved a culture temperature of 30° C., a stirring rate of 650 rpm, and an aeration rate of 8.1 L/min, with the pH controlled to range from 6.7 to 6.8. For controlling the pH, a 14% aqueous ammonium hydroxide solution was used. The carbon source was intermittently added. The carbon sources used are shown in Table 3. Palm olein oil was used as the fat and oil. The culture was carried out for 48 hrs, and after completing the culture, the cellular bodies were recovered by centrifugal separation, washed with methanol, freeze-dried and then the weight of dry cellular bodies was measured.
To about 1 g of thus obtained dry cellular bodies was added 100 ml of ethyl acetate, the mixture was stirred at room temperature overnight, and PHA in the cellular bodies was extracted. After the residue of the cellular bodies was filtered off, the extract was concentrated to give the total volume of about 30 ml with an evaporator. Then about 100 ml of methanol was gradually added to the concentrate, and precipitation of PHA was permitted by allowing to stand for 1 hour while gently stirring. Thus precipitated PHA was separated from methanol and ethyl acetate, and then vacuum dried at 50° C. for 3 hrs. The weight of the dry PHA was measured, and the content of PHA in the cellular bodies was calculated. The weight of the dry cellular bodies, the PHA content, and the amount of produced PHA are shown in Table 3.

tained that PHA produced in Example 3 was constituted with 3-hydroxyalkanoic acid monomers having 4 to 14 carbon atoms.

TABLE 3

| | | Fatty acid and fat and oil constitution of CS | | | | | Results of culture | | |
|---|---|---|---|---|---|---|---|---|---|
| | CS | LA content (wt %) | MA content (wt %) | PA content (wt %) | OA content (wt %) | Fat and oil content (wt %) | Ascending melting point (° C.) | Weight of dry cellular bodies (g/L) | PHA content (wt %) | Amount of produced PHA (g/L) |
| Comparative Example 3 | LA | 100 | 0 | 0 | 0 | 0 | 43 | 57.5 | 49.2 | 28.3 |
| | MA | 0 | 100 | 0 | 0 | 0 | 52 | 42.5 | 29.9 | 12.7 |
| | PA | 0 | 0 | 100 | 0 | 0 | 62 | 39.1 | 23.5 | 9.2 |
| | OA | 0 | 0 | 0 | 100 | 0 | 12 | 70.3 | 58.0 | 40.8 |
| | palmolein | 0 | 0 | 0 | 0 | 100 | 19 | 72.5 | 60.1 | 43.6 |
| Example 3 | CS 1 | 90 | 0 | 0 | 10 | 0 | 41 | 60.6 | 47.2 | 28.6 |
| | CS 2 | 50 | 0 | 0 | 50 | 0 | 27 | 71.5 | 56.6 | 40.5 |
| | CS 3 | 0 | 70 | 0 | 30 | 0 | 45 | 57.1 | 50.3 | 28.7 |
| | CS 4 | 0 | 50 | 0 | 50 | 0 | 37 | 65.4 | 53.4 | 34.9 |
| | CS 5 | 0 | 0 | 40 | 60 | 0 | 44 | 59.8 | 48.5 | 29.0 |
| | CS 6 | 0 | 0 | 20 | 80 | 0 | 27 | 71.3 | 56.4 | 40.2 |
| | CS 7 | 25 | 75 | 0 | 0 | 0 | 47 | 54.2 | 42.1 | 22.8 |
| | CS 8 | 75 | 25 | 0 | 0 | 0 | 34 | 69.5 | 57.7 | 40.1 |
| | CS 9 | 40 | 0 | 80 | 0 | 0 | 47 | 55.6 | 43.7 | 24.3 |
| | CS 10 | 75 | 0 | 25 | 0 | 0 | 37 | 69.5 | 58.7 | 40.8 |
| | CS 11 | 0 | 50 | 50 | 0 | 0 | 47 | 55.1 | 45.0 | 24.8 |
| | CS 12 | 0 | 0 | 47 | 53 | 0 | 45 | 58.8 | 48.3 | 28.4 |
| | CS 13 | 15 | 0 | 40 | 45 | 0 | 43 | 62.5 | 53.1 | 33.2 |
| | CS 14 | 60 | 0 | 19 | 21 | 0 | 32 | 71.5 | 57.8 | 41.3 |
| | CS 15 | 50 | 20 | 10 | 20 | 0 | 26 | 72.8 | 59.9 | 43.6 |
| | CS 16 | 25 | 10 | 30 | 35 | 0 | 36 | 71.1 | 56.5 | 40.2 |
| | CS 17 | 75 | 3 | 2 | 20 | 0 | 37 | 68.4 | 56.6 | 40.2 |
| | CS 18 | 0 | 0 | 45 | 50 | 5 | 44 | 58.7 | 49.9 | 29.3 |
| | CS 19 | 0 | 0 | 25 | 30 | 45 | 38 | 68.7 | 56.1 | 36.5 |
| | CS 20 | 0 | 0 | 19 | 21 | 55 | 34 | 70.1 | 57.7 | 40.4 |
| | CS 21 | 0 | 10 | 0 | 0 | 95 | 22 | 72.9 | 58.7 | 42.8 |
| | CS 22 | 0 | 0 | 10 | 0 | 95 | 23 | 71.4 | 58.2 | 41.6 |
| | CS 23 | 43 | 17 | 8 | 17 | 15 | 24 | 72.4 | 59.6 | 43.2 |
| | CS 24 | 21 | 9 | 27 | 33 | 10 | 34 | 70.8 | 57.8 | 40.9 |
| | CS 25 | 28 | 9 | 18 | 26 | 19 | 28 | 72.2 | 58.1 | 41.9 |

LA: Lauric acid,
MA: Myristic acid,
PA: Palmitic acid,
OA: Oleic acid,
CS: Carbon source The monomer composition of the produced PHA was analyzed with gas chromatography as follows. To about 20 mg of dry PHA were added 2 ml of a mixture of sulfuric acid and methanol (15:85) and 2 ml of chloroform. The system was tightly stopped, and heated at 100° C. for 140 min to afford a methyl ester of the degradation product of PHA. After cooling, small amounts of aliquots of 1.5 g of sodium bicarbonate were added thereto to neutralize the mixture, and left to stand until generation of carbon dioxide gas ceases. After adding 4 ml of diisopropyl ether thereto and mixing well, centrifugation was carried out. The monomer composition of the degradation product of PHA in the supernatant was analyzed by capillary gas chromatography. GC-17A manufactured by Shimadzu Corporation was used for the gas chromatography, and the capillary column employed was NEUTRA BOND-1 manufactured by GL Sciences Inc., (column length: 25 m; column internal diameter: 0.25 mm, and liquid film thickness: 0.4 μm). He gas was used as the carrier gas, with a column inlet pressure of 100 kPa. The sample was injected in a volume of 1 μl. The temperature conditions involved: an initial temperature of 100° C.; temperature elevation from 100° C. to 200° C. at a rate of 8° C./min; and additional temperature elevation from 200° C. to 290° C. at a rate of 30° C./min. As a result of analysis under the aforementioned conditions, it was ascer- Comparative Example 3

The *Pseudomonas resinovorans* ATCC 14235 strain was cultured under the same conditions as in Example 3 except that lauric acid, myristic acid, palmitic acid, oleic acid or palm olein oil was used alone as a carbon source in place of the various types of fatty acid composition or mixed composition, and the weight of dry cellular bodies, the PHA content, and the amount of produced PHA were measured. The results are shown in Table 3.

Example 4

Production of PHA by Culture of *C. maltosa*

Using a variety of carbon sources, PHA was produced by culturing the microorganism.

The microorganism used was a *C. maltosa* AHU-71 pARR-149/171NSx2-phbB strain (see PCT International Publication No. 2005/085415).

A YNB medium (0.67 w/v % Yeast Nitrogen base without amino acid, and 2 w/v % Glucose) was used as the preculture medium. A medium prepared by adding a 0.45 ml/L trace mineral salt solution (1 g/mL $FeSO_4.7H_2O$, 8 g/mL $ZnSO_4.7H_2O$, 6.4 g/mL $MnSO_4.4H_2O$ and 0.8 g/mL $CuSO_4.5H_2O$ dissolved in 0.1 N hydrochloric acid) to a M2 medium (12.75 g/L (NH$_4$)$_2$SO$_4$, 1.56 g/L KH$_2$PO$_4$, 0.33 g/L K$_2$HPO$_4$.3H$_2$O, 0.08 g/L KCl, 0.5 g/L NaCl, 0.41 g/L MgSO$_4$.7H$_2$O, 0.4 g/L Ca (NO$_2$)$_2$.4H$_2$O and 0.01 g/L FeCl$_3$.4H$_2$O) was used as the production medium of PHA.

A glycerol stock of the *C. maltosa* AHU-71 pARR-149/171NSx2-phbB strain was inoculated in a volume of 500 µl into a 500-ml Sakaguchi flask containing 50 ml of the preculture medium, and cultured at a culture temperature of 30° C. for 20 hrs. Thus obtained culture liquid was inoculated at 10 v/v % into a 2-L Sakaguchi flask containing 3.00 ml of the production medium of PHA. Moreover, various types of fatty acid compositions or mixed compositions shown in Table 4 were each charged as a carbon source into the Sakaguchi flask at a concentration of 2 w/v %, and the mixture was cultured by shaking at 30° C. for 48 hrs. The carbon source was added batchwise into the Sakaguchi flask. After completing the culture, the cellular bodies were recovered by centrifugal separation, washed with methanol, freeze-dried, and then the weight of dry cellular bodies was measured.

To about 1 g of thus obtained dry cellular bodies was added 100 ml of chloroform, the mixture was stirred at room temperature overnight, and PHA in the cellular bodies was extracted. After the residue of the cellular bodies was filtered off, the extract was concentrated to give the total volume of about 30 ml with an evaporator. Then about 90 ml of hexane was gradually added to the concentrate, and precipitation of PHA was permitted by allowing to stand for 1 hour while gently stirring. Thus precipitated PHA was filtered off, and then vacuum dried at 50° C. for 3 hrs. The weight of the dry PHA was measured, and the content of PHA in the cellular bodies was calculated. The weight of the dry cellular bodies, the PHA content, and the amount of produced PHA are shown in Table 4.

TABLE 4

| | | Fatty acid and fat and oil constitution of CS | | | | | Results of culture | | |
|---|---|---|---|---|---|---|---|---|---|
| | CS | LA content (wt %) | MA content (wt %) | PA content (wt %) | OA content (wt %) | Fat and oil content (wt %) | Ascending melting point (° C.) | Weight of dry cellular bodies (g/L) | PHA content (wt %) | Amount of produced PHA (g/L) |
| Comparative Example 4 | LA | 100 | 0 | 0 | 0 | 0 | 43 | 7.9 | 40.1 | 3.2 |
| | MA | 0 | 100 | 0 | 0 | 0 | 52 | 4.8 | 39.2 | 1.9 |
| | PA | 0 | 0 | 100 | 0 | 0 | 62 | 3.9 | 39.4 | 1.5 |
| | OA | 0 | 0 | 0 | 100 | 0 | 12 | 10.8 | 40.2 | 4.3 |
| | palmolein | 0 | 0 | 0 | 0 | 100 | 19 | 11.0 | 40.6 | 4.5 |
| Example 4 | CS 1 | 90 | 0 | 0 | 10 | 0 | 41 | 8.7 | 40.1 | 3.5 |
| | CS 2 | 50 | 0 | 0 | 50 | 0 | 27 | 10.2 | 41.2 | 4.2 |
| | CS 3 | 0 | 70 | 0 | 30 | 0 | 45 | 7.8 | 39.1 | 3.0 |
| | CS 4 | 0 | 50 | 0 | 50 | 0 | 37 | 9.4 | 40.7 | 3.8 |
| | CS 5 | 0 | 0 | 40 | 60 | 0 | 44 | 8.2 | 40.5 | 3.3 |
| | CS 6 | 0 | 0 | 20 | 80 | 0 | 27 | 10.6 | 40.3 | 4.3 |
| | CS 7 | 25 | 75 | 0 | 0 | 0 | 47 | 7.1 | 39.7 | 2.8 |
| | CS 8 | 75 | 25 | 0 | 0 | 0 | 34 | 9.8 | 41.2 | 4.0 |
| | CS 9 | 40 | 0 | 60 | 0 | 0 | 47 | 6.4 | 39.8 | 2.5 |
| | CS 10 | 75 | 0 | 25 | 0 | 0 | 37 | 9.9 | 40.7 | 4.0 |
| | CS 11 | 0 | 50 | 50 | 0 | 0 | 47 | 6.9 | 38.9 | 2.7 |
| | CS 12 | 0 | 0 | 47 | 53 | 0 | 45 | 8.0 | 40.1 | 3.2 |
| | CS 13 | 15 | 0 | 40 | 45 | 0 | 43 | 8.2 | 41.2 | 3.4 |
| | CS 14 | 60 | 0 | 19 | 21 | 0 | 32 | 10.5 | 40.6 | 4.3 |
| | CS 15 | 50 | 20 | 10 | 20 | 0 | 26 | 11.1 | 41.1 | 4.6 |
| | CS 16 | 25 | 10 | 30 | 35 | 0 | 36 | 10.8 | 40.1 | 4.3 |
| | CS 17 | 75 | 3 | 2 | 20 | 0 | 37 | 9.9 | 39.4 | 3.9 |
| | CS 18 | 0 | 0 | 45 | 50 | 5 | 44 | 8.1 | 39.8 | 3.2 |
| | CS 19 | 0 | 0 | 25 | 30 | 45 | 38 | 10.0 | 38.4 | 3.8 |
| | CS 20 | 0 | 0 | 19 | 21 | 55 | 34 | 10.2 | 40.2 | 4.1 |
| | CS 21 | 0 | 10 | 0 | 0 | 90 | 22 | 11.2 | 40.6 | 4.5 |
| | CS 22 | 0 | 0 | 10 | 0 | 90 | 23 | 10.9 | 40.2 | 4.4 |
| | CS 23 | 43 | 17 | 8 | 17 | 15 | 24 | 11.1 | 40.6 | 4.5 |
| | CS 24 | 21 | 9 | 27 | 33 | 10 | 34 | 10.2 | 40.2 | 4.1 |
| | CS 25 | 28 | 9 | 18 | 26 | 19 | 28 | 11.1 | 40.7 | 4.5 |

LA: Lauric acid,
MA: Myristic acid,
PA: Palmitic acid,
OA: Oleic acid,
CS: Carbon source The monomer composition of the produced PHA was analyzed with a similar method to Example 3. As a result, it was ascertained that PHA produced in Example 4 was a copolymer (PHBH) of 3-hydroxybutyric acid having 4 carbon atoms and 3-hydroxyhexanoic acid having 6 carbon atoms.

Comparative Example 4

The *C. maltosa* AHU-71 pARR-149/171NSx2-phbB strain was cultured under the same conditions as in Example 4 except that lauric acid, myristic acid, palmitic acid, oleic acid or palm olein oil was used as a carbon source in place of the various types of fatty acid composition or mixed composition, and the weight of dry cellular bodies, the PHA content, and the amount of produced PHA were measured. The results are shown in Table 4.

Example 5

Production of PHA by Culture of KNK-005 Strain

The microorganism used was a KNK-005 strain (see U.S. Pat. No. 7,384,766).

The composition of the mother culture medium was constituted with 1 w/v % Meat-extract, 1 w/v % Bacto-tryptone, 0.2 w/v % Yeast-extract, 0.9 w/v % Na$_2$HPO$_4$.12H$_2$O and 0.15 w/v % KH$_2$PO$_4$, and the pH was adjusted to 6.8.

The composition of the preculture medium was constituted with 1.1 w/v % Na$_2$HPO$_4$.12H$_2$O, 0.19 w/v % KH$_2$PO$_4$, 1.29 w/v % (NH$_4$)$_2$SO$_4$, 0.1 w/v % MgSO$_4$.7H$_2$O, 2.5 w/v % palm olein oil and a 0.5 v/v % trace mineral salt solution (1.6 w/v % FeCl$_3$.6H$_2$O, 1 w/v % CaCl$_2$.2H$_2$O, 0.02 w/v % CoCl$_2$.6H$_2$O, 0.016 w/v % CuSO$_4$.5H$_2$O and 0.012 w/v % NiCl$_2$.6H$_2$O dissolved in 0.1 N hydrochloric acid). Palm olein oil as a carbon source in the preculture medium was added batchwise at a concentration of 10 g/L.

The composition of the production medium of PHA was constituted with 0.385 w/v % Na$_2$HPO$_4$.12H$_2$O, 0.067 w/v % KH$_2$PO$_4$, 0.291 w/v % (NH$_4$)$_2$SO$_4$, 0.1 w/v % MgSO$_4$.7H$_2$O, a 0.5 v/v % trace mineral salt solution (1.6 w/v % FeCl$_3$.6H$_2$O, 1 w/v % CaCl$_2$.2H$_2$O, 0.02 w/v % CoCl$_2$.6H$_2$O, 0.016 w/v % CuSO$_4$.5H$_2$O and 0.012 w/v % NiCl$_2$.6H$_2$O dissolved in 0.1 N hydrochloric acid), and 0.05 w/v % BIOSPUREX 200K (defoaming agent: manufactured by Cognis Japan Ltd.).

First, a glycerol stock (50 µl) of the KNK-005 strain was inoculated into the mother culture medium (10 ml), and cultured for 24 hrs to execute mother culture. Next, the mother culture liquid was inoculated at 1.0 v/v % into a 3-L jar fermenter (manufactured by B. E. MARUBISHI Co., Ltd., model MDL-300) containing 1.8 L of the preculture medium. The operating conditions involved a culture temperature of 33° C., a stirring rate of 500 rpm, and an aeration rate of 1.8 L/min. The preculture was executed by culturing for 28 hrs while controlling the pH to range from 6.7 to 6.8. For controlling the pH, a 14% aqueous ammonium hydroxide solution was used.

Next, the preculture liquid was inoculated at 5.0 v/v % into a 5-L jar fermenter (manufactured by B. E. MARUBISHI Co., Ltd., model MDS-U50) containing 2.5 L of the production medium. The operating conditions involved a culture temperature of 33° C., a stirring rate of 420 rpm, and an aeration rate of 2.1 L/min, with the pH controlled to range from 6.7 to 6.8. For controlling the pH, a 14% aqueous ammonium hydroxide solution was used. The carbon source was intermittently added. The carbon sources used are shown in Table 5. Palm olein oil was used as the fat and oil. The culture was carried out for 64 hrs, and after completing the culture, the cellular bodies were recovered by centrifugal separation, washed with methanol, freeze-dried and then the weight of dry cellular bodies was measured.

To 1 g of thus obtained dry cellular bodies was added 100 ml of chloroform, the mixture was stirred at room temperature overnight, and PHA in the cellular bodies was extracted. After the residue of the cellular bodies was filtered off, the extract was concentrated to give the total volume of 30 ml with an evaporator. Thereafter, 90 ml of hexane was gradually added to the concentrate, and precipitation of PHA was permitted by allowing to stand for 1 hour while gently stirring. Thus precipitated PHA was filtered off, and then vacuum dried at 50° C. for 3 hrs. The weight of the dry PHA was measured, and the content of PHA in the cellular bodies was calculated. The weight of the dry cellular bodies, the PHA content, and the amount of produced PHA are shown in Table 5.

The monomer composition of the produced PHA was analyzed with a similar method to Example 3. As a result, it was ascertained that PHA produced in Example 5 was a copolymer (PHBH) of 3-hydroxybutyric acid having 4 carbon atoms and 3-hydroxyhexanoic acid having 6 carbon atoms.

TABLE 5

| | | Fatty acid and fat and oil constitution of CS | | | | | Results of culture | | |
|---|---|---|---|---|---|---|---|---|---|---|
| | CS | LA content (wt %) | MA content (wt %) | PA content (wt %) | OA content (wt %) | Fat and oil content (wt %) | Ascending melting point (° C.) | Weight of dry cellular bodies (g/L) | PHA content (wt %) | Amount of produced PHA (g/L) |
| Comparative Example 5 | LA | 100 | 0 | 0 | 0 | 0 | 43 | 121.5 | 65.1 | 79.1 |
| | MA | 0 | 100 | 0 | 0 | 0 | 52 | 67.3 | 34.9 | 23.5 |
| | PA | 0 | 0 | 100 | 0 | 0 | 62 | 60.1 | 33.4 | 20.1 |
| | OA | 0 | 0 | 0 | 100 | 0 | 12 | 145.9 | 75.8 | 110.6 |
| | palmolein | 0 | 0 | 0 | 0 | 100 | 19 | 149.6 | 75.6 | 113.1 |
| Example 5 | CS 1 | 90 | 0 | 0 | 10 | 0 | 41 | 130.1 | 70.1 | 91.2 |
| | CS 2 | 50 | 0 | 0 | 50 | 0 | 27 | 146.1 | 76.2 | 111.3 |
| | CS 3 | 0 | 70 | 0 | 30 | 0 | 45 | 100.3 | 48.1 | 48.2 |
| | CS 4 | 0 | 50 | 0 | 50 | 0 | 37 | 134.1 | 71.2 | 95.5 |
| | CS 5 | 0 | 0 | 40 | 60 | 0 | 44 | 115.0 | 65.4 | 75.2 |
| | CS 6 | 0 | 0 | 20 | 80 | 0 | 27 | 144.9 | 75.1 | 108.8 |
| | CS 7 | 25 | 75 | 0 | 0 | 0 | 47 | 89.1 | 46.8 | 41.7 |
| | CS 8 | 75 | 25 | 0 | 0 | 0 | 34 | 143.5 | 74.9 | 107.5 |
| | CS 9 | 40 | 0 | 60 | 0 | 0 | 47 | 90.1 | 47.3 | 42.6 |
| | CS 10 | 75 | 0 | 25 | 0 | 0 | 37 | 140.1 | 73.2 | 102.6 |
| | CS 11 | 0 | 50 | 50 | 0 | 0 | 47 | 92.4 | 47.4 | 43.8 |
| | CS 12 | 0 | 0 | 47 | 53 | 0 | 45 | 113.4 | 60.9 | 69.1 |
| | CS 13 | 15 | 0 | 40 | 45 | 0 | 43 | 138.1 | 72.6 | 100.3 |
| | CS 14 | 60 | 0 | 19 | 21 | 0 | 32 | 146.0 | 77.1 | 112.6 |
| | CS 15 | 50 | 20 | 10 | 20 | 0 | 26 | 147.5 | 75.9 | 112.0 |
| | CS 16 | 25 | 10 | 30 | 35 | 0 | 36 | 148.1 | 75.7 | 112.1 |
| | CS 17 | 75 | 3 | 2 | 20 | 0 | 37 | 144.4 | 74.1 | 107.0 |
| | CS 18 | 0 | 0 | 45 | 50 | 5 | 44 | 125.7 | 65.8 | 82.7 |
| | CS 19 | 0 | 0 | 25 | 30 | 45 | 38 | 143.7 | 75.4 | 108.3 |
| | CS 20 | 0 | 0 | 19 | 21 | 55 | 34 | 145.3 | 75.9 | 110.3 |
| | CS 21 | 0 | 10 | 0 | 0 | 90 | 22 | 150.4 | 76.0 | 114.3 |
| | CS 22 | 0 | 0 | 10 | 0 | 90 | 23 | 148.7 | 75.2 | 111.8 |

TABLE 5-continued

| | Fatty acid and fat and oil constitution of CS | | | | | Results of culture | | | |
|---|---|---|---|---|---|---|---|---|---|
| CS | LA content (wt %) | MA content (wt %) | PA content (wt %) | OA content (wt %) | Fat and oil content (wt %) | Ascending melting point (° C.) | Weight of dry cellular bodies (g/L) | PHA content (wt %) | Amount of produced PHA (g/L) |
| CS 23 | 43 | 17 | 8 | 17 | 15 | 24 | 146.9 | 76.5 | 112.4 |
| CS 24 | 21 | 9 | 27 | 33 | 10 | 34 | 147.0 | 75.9 | 111.6 |
| CS 25 | 28 | 9 | 18 | 26 | 19 | 28 | 147.3 | 75.5 | 111.2 |

LA: Lauric acid,
MA: Myristic acid,
PA: Palmitic acid,
OA: Oleic acid,
CS: Carbon source Comparative Example 5

The KNK-005 strain was cultured under the same conditions as in Example 5 except that lauric acid, myristic acid, palmitic acid, oleic acid and palm olein oil were used as a carbon source in place of the various types of fatty acid composition or mixed composition, and the weight of dry cellular bodies, the PHA content, and the amount of produced PHA were measured. The results are shown in Table 5.

Example 6

Verification of Possible Increase in Scale Using Carbon Sources 19, 23, 24 and 25 in Example 5

Possible increase in scale was verified using the carbon sources (carbon sources 19, 23, 24 and 25) containing a plurality of long chain fatty acids, and a fat and oil that demonstrated in Example 5 improvement of the amount of microorganism growth and the amount of produced PHA as compared with use of the long chain saturated fatty acid alone.

The microorganism used was a KNK-005 strain, similarly to Example 5.

The composition of the mother culture medium (primary and secondary culture) was constituted with 1 w/v % Meat-extract, 1 w/v % Bacto-tryptone, 0.2 w/v % Yeast-extract, 0.9 w/v % $Na_2HPO_4 \cdot 12H_2O$ and 0.15 w/v % $KH_2PO_4$, and the pH was adjusted to 6.8.

The composition of the preculture medium was constituted with 1.1 w/v % $Na_2HPO_4 \cdot 12H_2O$, 0.19 w/v % $KH_2PO_4$, 1.29 w/v % $(NH_4)_2SO_4$, 0.1 w/v % $MgSO_4 \cdot 7H_2O$, 2.5 w/v % palm olein oil and a 0.5 v/v % trace mineral salt solution (1.6 w/v % $FeCl_3 \cdot 6H_2O$, 1 w/v % $CaCl_2 \cdot 2H_2O$, 0.02 w/v % $CoCl_2 \cdot 6H_2O$, 0.016 w/v % $CuSO_4 \cdot 5H_2O$ and 0.012 w/v % $NiCl_2 \cdot 6H_2O$ dissolved in 0.1 N hydrochloric acid). Palm olein oil as a carbon source in the preculture medium was added batchwise at a concentration of 10 g/L.

The composition of the production medium of PHA was constituted with 0.385 w/v % $Na_2HPO_4 \cdot 12H_2O$, 0.067 w/v % $KH_2PO_4$, 0.291 w/v % $(NH_4)_2SO_4$, 0.1 w/v % $MgSO_4 \cdot 7H_2O$, a 0.5 v/v % trace mineral salt solution (1.6 w/v % $FeCl_3 \cdot 6H_2O$, 1 w/v % $CaCl_2 \cdot 2H_2O$, 0.02 w/v % $CoCl_2 \cdot 6H_2O$, 0.016 w/v % $CuSO_4 \cdot 5H_2O$ and 0.012 w/v % $NiCl_2 \cdot 6H_2O$ dissolved in 0.1 N hydrochloric acid), and 0.05 w/v % BIOSPUREX 200K (defoaming agent: manufactured by Cognis Japan Ltd.).

For primary culture, 500 μl of a glycerol stock of the KNK-005 strain was first inoculated into a 500-ml Sakaguchi flask containing 50 ml of the mother culture medium, and cultured at a culture temperature of 30° C. for 20 hrs. Next, for secondary culture, the primary culture liquid was inoculated at 10 v/v % into a 2-L Sakaguchi flask containing 500 ml of the mother culture medium, and cultured at a culture temperature of 30° C. for 24 hrs. Subsequently, for the mother culture, the secondary culture liquid was inoculated at 1.0 v/v % into a culture bath having a volume of 1,000 L containing 400 L of the preculture medium. The operating conditions involved a culture temperature of 33° C., a stirring rate of 270 rpm, and an aeration rate of 200 L/min. The preculture was executed by culturing for 24 hrs while controlling the pH to range from 6.7 to 6.8. For controlling the pH, a 14% aqueous ammonium hydroxide solution was used.

Next, for main culture, the preculture liquid was inoculated at 2.5 v/v % into a culture bath having a volume of 400,000 L containing 16,000 L of the production medium of PHA. The operating conditions involved a culture temperature of 33° C., a stirring rate of 86 rpm, and an aeration rate of 5,000 L/min, with the pH controlled to range from 6.7 to 6.8. For controlling the pH, a 14% aqueous ammonium hydroxide solution was used. The carbon source was intermittently added. The culture was carried out for 65 hrs, and after completing the culture, the cellular bodies were recovered by centrifugal separation, washed with methanol, freeze-dried and then the weight of dry cellular bodies was measured.

To 1 g of thus obtained dry cellular bodies was added 100 ml of chloroform, the mixture was stirred at room temperature overnight, and PHA in the cellular bodies was extracted. After the residue of the cellular bodies was filtered off, the extract was concentrated to give the total volume of 30 ml with an evaporator. Thereafter, 90 ml of hexane was gradually added to the concentrate, and precipitation of PHA was permitted by allowing to stand for 1 hour while gently stirring. Thus precipitated PHA was filtered off, and then vacuum dried at 50° C. for 3 hrs. The weight of the dry PHA was measured, and the content of PHA in the cellular bodies was calculated. The weight of the dry cellular bodies, the PHA content, and the amount of produced PHA are shown in Table 6.

TABLE 6

| | | Fatty acid and fat and oil constitution of CS | | | | Results of culture | | |
|---|---|---|---|---|---|---|---|---|
| | CS | LA content (wt %) | MA content (wt %) | PA content (wt %) | OA content (wt %) | Fat and oil content (wt %) | Weight of dry cellular bodies (g/L) | PHA content (wt %) | Amount of produced PHA (g/L) |
| Example 6 | CS 19 | 0 | 0 | 25 | 30 | 45 | 144.9 | 75.8 | 109.8 |
| | CS 23 | 43 | 17 | 8 | 17 | 15 | 149.1 | 77.5 | 115.6 |
| | CS 24 | 21 | 9 | 27 | 33 | 10 | 148.5 | 76.4 | 113.5 |
| | CS 25 | 28 | 9 | 18 | 26 | 19 | 148.2 | 75.5 | 111.9 |

LA: Lauric acid,
MA: Myristic acid,
PA: Palmitic acid,
OA: Oleic acid,
CS: Carbon source

The invention claimed is:

1. A method for culturing a microorganism comprising culturing a microorganism in the presence of a carbon source comprising any one of the following compositions:
   (1) a free fatty acid composition comprising free lauric acid at a content of 30 to 70% by weight, free myristic acid at a content of 5 to 30% by weight, free palmitic acid at a content of 5 to 30% by weight, and free oleic acid at a content of 10 to 30% by weight; and
   (2) a mixed composition comprising a fat and oil, and free lauric acid at a content of 30 to 70% by weight (the value excluding the fat and oil), free myristic acid at a content of 5 to 30% by weight (the value excluding the fat and oil), free palmitic acid at a content of 5 to 30% by weight (the value excluding the fat and oil), free oleic acid at a content of 10 to 30% by weight (the value excluding the fat and oil), wherein the total content of the free fatty acids in the mixed composition is not less than 50% by weight, wherein the free fatty acids do not include the moiety from the fatty acid constituting the fat and oil.

2. The culture method according to claim 1, wherein the free fatty acid composition or the mixed composition has an ascending melting point of not higher than a temperature that is greater than the culture temperature by 10° C.

3. The culture method according to claim 1, wherein the microorganism is a bacterium.

4. The culture method according to claim 3, wherein the microorganism is a microorganism belonging to genus *Cupriavidus* or genus *Esherichia*.

5. The culture method according to claim 4, wherein the microorganism is a microorganism belonging to genus *Cupriavidus*.

6. The culture method according to claim 5, wherein the microorganism is *Cupriavidus necator*.

7. The culture method according to claim 6, wherein the microorganism is *Cupriavidus necator* incorporating:
   a polyhydroxyalkanoate synthase gene encoding an amino acid sequence shown in SEQ ID NO: 1; or
   a polyhydroxyalkanoate synthase gene encoding a polypeptide having a sequence identity to said amino acid sequence of not less than 85%, and having a synthetic activity of polyhydroxyalkanoate.

8. The culture method according to claim 4, wherein the microorganism is a microorganism belonging to genus *Esherichia*.

9. The culture method according to claim 8, wherein the microorganism is *Esherichia coli* is *Esherichia coli*.

10. The culture method according to claim 1, wherein the microorganism is yeast.

11. A method for producing a metabolic product of a microorganism, the method comprising culturing the microorganism in the presence of a carbon source comprising any of the following compositions:
   (1) a free fatty acid composition comprising free lauric acid at a content of 30 to 70% by weight, free myristic acid at a content of 5 to 30% by weight, free palmitic acid at a content of 5 to 30% by weight, and free oleic acid at a content of 10 to 30% by weight; and
   (2) a mixed composition comprising a fat and oil, and free lauric acid at a content of 30 to 70% by weight (the value excluding the fat and oil), free myristic acid at a content of 5 to 30% by weight (the value excluding the fat and oil), free palmitic acid at a content of 5 to 30% by weight (the value excluding the fat and oil), free oleic acid at a content of 10 to 30% by weight (the value excluding the fat and oil), wherein the total content of the free fatty acids in the mixed composition is not less than 50% by weight, wherein the free fatty acids do not include the moiety from the fatty acid constituting the fat and oil, and
   recovering the metabolic product produced by the microorganism cultured.

12. The method according to claim 11, wherein the metabolic product of the microorganism is polyhydroxyalkanoate.

13. The method according to claim 12, wherein the polyhydroxyalkanoate is a copolymer of 3-hydroxybutyric acid and 3-hydroxyhexanoic acid.

* * * * *